United States Patent
Yamazaki et al.

(10) Patent No.: US 6,790,205 B1
(45) Date of Patent: Sep. 14, 2004

(54) LASER BEAM PROJECTOR

(75) Inventors: Iwao Yamazaki, Tokyo (JP); Yoshihiro Izawa, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 60 days.

(21) Appl. No.: 10/203,647

(22) PCT Filed: Sep. 27, 2000

(86) PCT No.: PCT/JP00/06670

§ 371 (c)(1),
(2), (4) Date: Aug. 23, 2002

(87) PCT Pub. No.: WO01/64285

PCT Pub. Date: Sep. 7, 2001

(30) Foreign Application Priority Data

Mar. 1, 2000 (JP) .................................. P2000-055264

(51) Int. Cl.[7] .............................................. A61B 18/20
(52) U.S. Cl. ............................... 606/9; 606/11; 607/89
(58) Field of Search .................. 606/2–13; 607/88–94

(56) References Cited

U.S. PATENT DOCUMENTS

| | | | | |
|---|---|---|---|---|
| 5,860,967 A | * | 1/1999 | Zavislan et al. | 606/9 |
| 5,868,731 A | * | 2/1999 | Budnik et al. | 606/9 |
| 6,210,425 B1 | * | 4/2001 | Chen | 607/88 |
| 6,383,177 B1 | * | 5/2002 | Balle-Petersen et al. | 606/9 |
| 6,436,127 B1 | * | 8/2002 | Anderson et al. | 607/89 |

FOREIGN PATENT DOCUMENTS

JP 11-332879 * 5/1998 ............ A61B/17/36

* cited by examiner

Primary Examiner—Roy D. Gibson
Assistant Examiner—Henry M. Johnson, III
(74) Attorney, Agent, or Firm—Bacon & Thomas, PLLC

(57) ABSTRACT

A laser beam projector equipped with a CCD camera for taking a picture of a spot for treatment, thus permitting observation of the spot by sight. The laser beam projector has an annular projection formed around a circular hole made on the front of its casing, and a trapezoid heat sink is fitted in the circular hole with its base caught by the circumference of the annular projection. The annular projection has threads formed on its outer circumference. A tapered cap has a laser beam throwing aperture made on its top end. The tapered cap is screwed and fixed to the annular projection, and the tapered head is applied to the spot with the laser beam aperture closed with the skin. The heat sink has a through hole made at its center, and a magnifying lens is placed deep in the through hole, and is directed to the laser beam throwing aperture. The CCD camera is placed behind the magnifying lens with its focal plan aligned with the lens. Another through hole is made above the through hole at an oblique angle relative to the center line of the heat sink. A spherical lens is fitted in the open end of the oblique through hole, and the spherical lens is directed at the laser beam throwing aperture. A laser diode is placed behind the spherical lens. A plurality of through holes are made around the center through hole, and a high-intensity, white light emitting diode is inserted in each through hole.

3 Claims, 3 Drawing Sheets

LASER BEAM PROJECTOR

TECHNICAL FIELD

The present invention relates to a laser beam projector for projecting a laser beam to a selected area on the skin for depilation or skin treatment.

BACKGROUND ART

Unwanted hair is removed from the body by applying depilatory cream to a selected area on the skin, and then, the depilatory area is exposed to a laser beam to allow melanin within the skin to absorb the very hot narrow beam of light, thereby causing protein denaturation in the skin texture by heating.

Thus, sebaceous glands and hair roots are damaged to harden the hair follicle texture. As a result the growth of hair is suppressed.

When a laser beam is projected to discolored pigment cells scattered in the outer or inner skin in the form of spots or freckles, they are heated to be divided in minute particles.

Discolored pigment cells thus divided come up to the skin surface, or otherwise, such minute particles are absorbed as waste products in blood vessels or lymphatic vessels. Finally, discolored pigment cells disappear from the skin, which remains free of unpleasing spots or freckles.

Depilation or skin treatment using a laser beam requires that pores of the skin or discolored pigment cells be exposed to the very hot narrow beam of light with accuracy because otherwise, a satisfactory treatment can be hardly attained.

A conventional laser projector, however, prevents location of such pores or discolored pigment cells by sight because they are hidden by the laser projector.

Therefore, the laser beam is apt to hit-the target with a reduced probability, causing the surrounding area on the skin to be exposed unnecessarily to the laser beam. Such a near miss is the cause for damaging the surrounding area on the skin.

Also, it is possible that the laser beam starts projecting before the laser beam projector is applied to the skin, and there is the possibility that the laser beam will strike the person's eye.

The object of the present invention is to provide a laser beam projector equipped with a CCD camera for taking a picture of a right spot on the skin, thereby permitting location of the target on the skin by sight.

SUMMARY OF THE INVENTION

To attain the object noted a laser beam projector is constructed to include: a head to be applied to the skin, the head having a switch attached at its tip for detecting that the head is in contact with the skin, a laser beam aperture formed in its tip and a through hole which opens to the laser beam aperture; a CCD camera situated to be directed at the through hole; a semiconductor laser source placed in the head so that the laser beam may pass through a condenser lens ahead of the laser source to coverge at the laser beam aperture; and an illumination source situated in the head to illuminate the laser beam aperture.

A laser beam projector is constructed according to claim 2 as follows: it further includes, in its casing, a drive circuit for the semiconductor laser source and a video signal processing circuit for the CCD camera.

A laser beam projector is constructed according to claim 3 as follows: it further comprises a connector for providing a home television with the images taken by the CCD camera.

A laser beam projector is constructed according to claim 4 as follows: it further comprises a cooling fan placed behind the heat sink.

DETAILED DESCRIPTION OF THE PREFERRED EMBODIMENT

Figure 1:
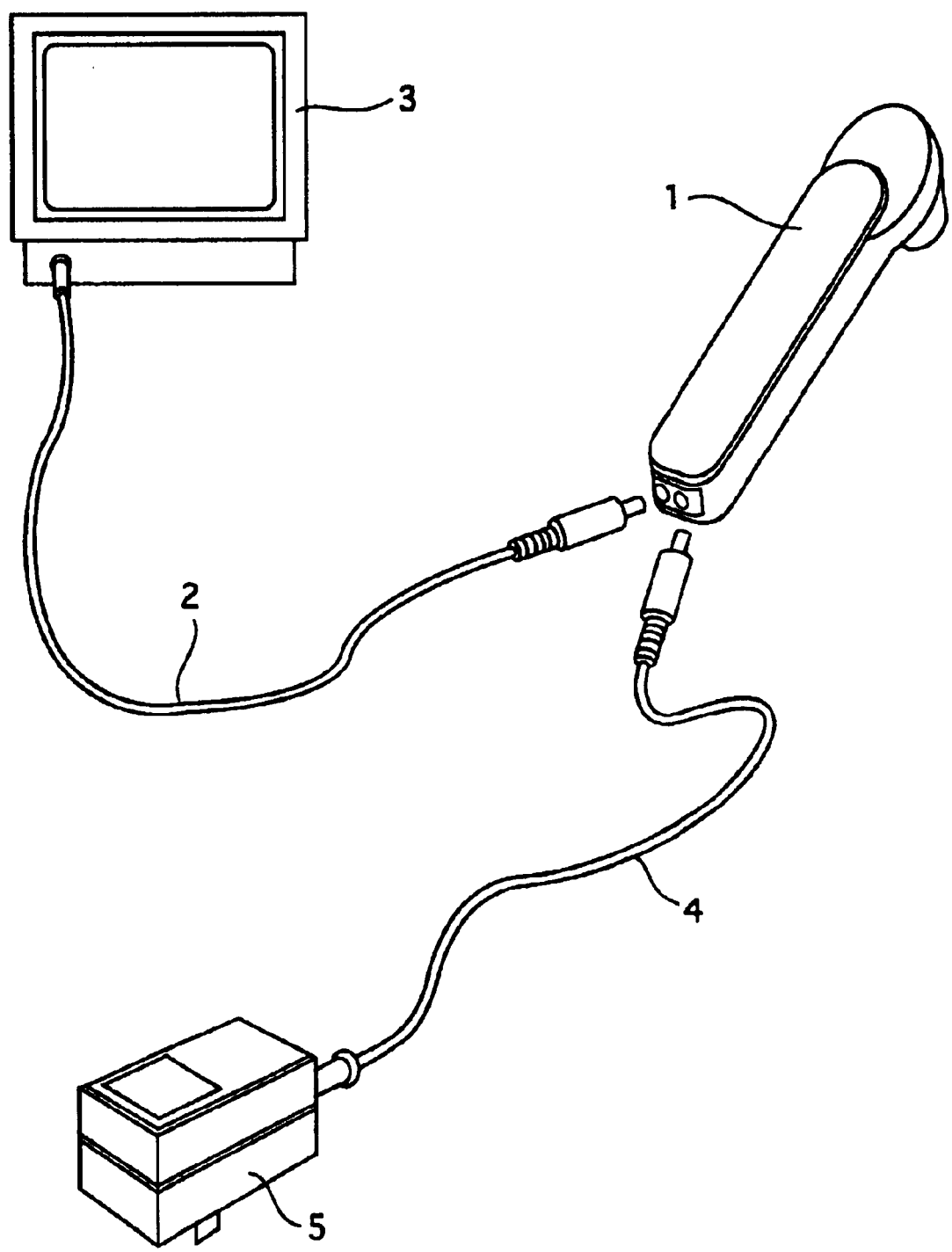
FIG. 1 is a perspective view of a laser beam projector according to the present invention along with an AC adapter and a home television.
Figure 2:
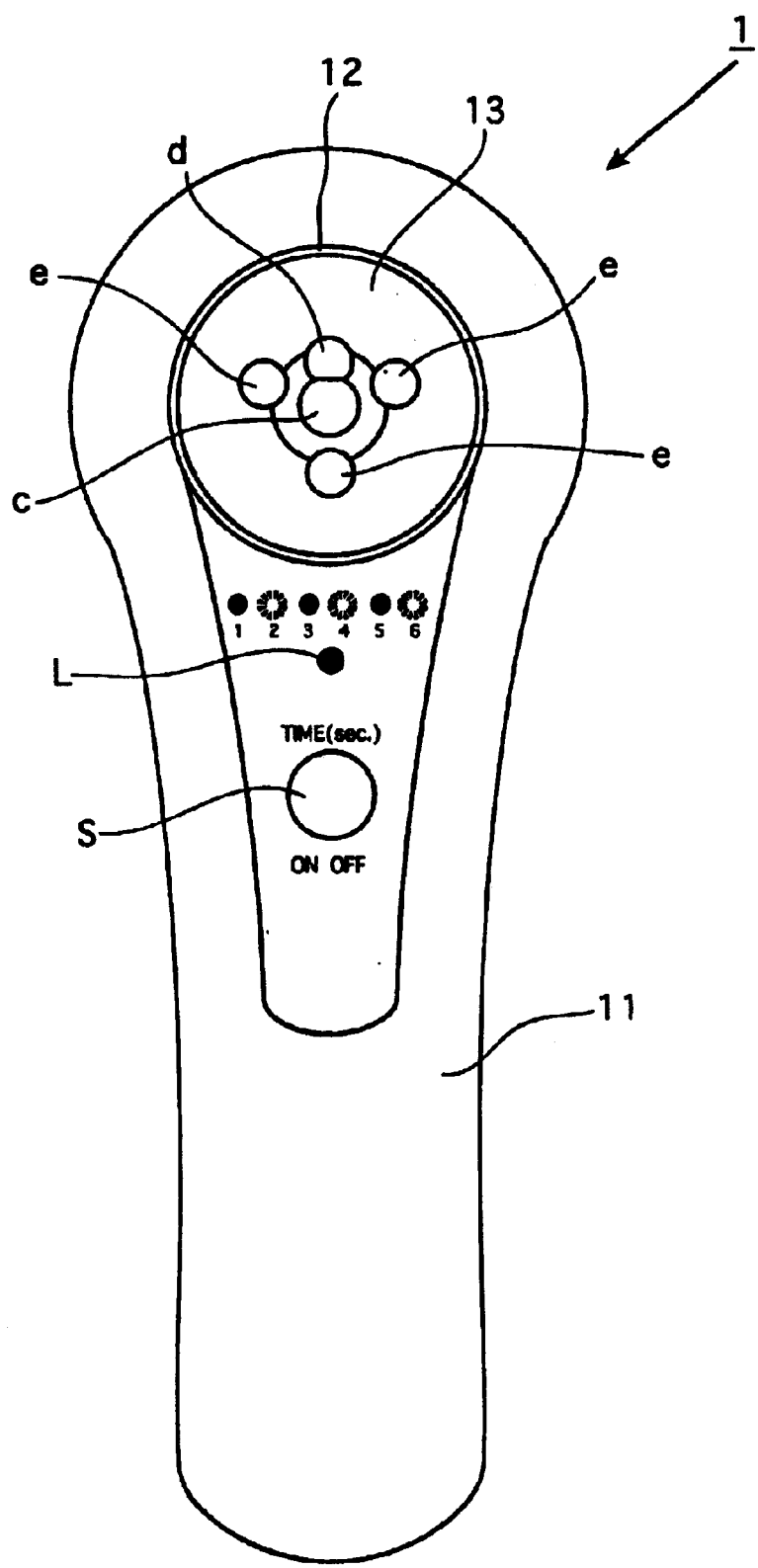
FIG. 2 is a front view of the laser beam projector with its cap removed.
Figure 3:
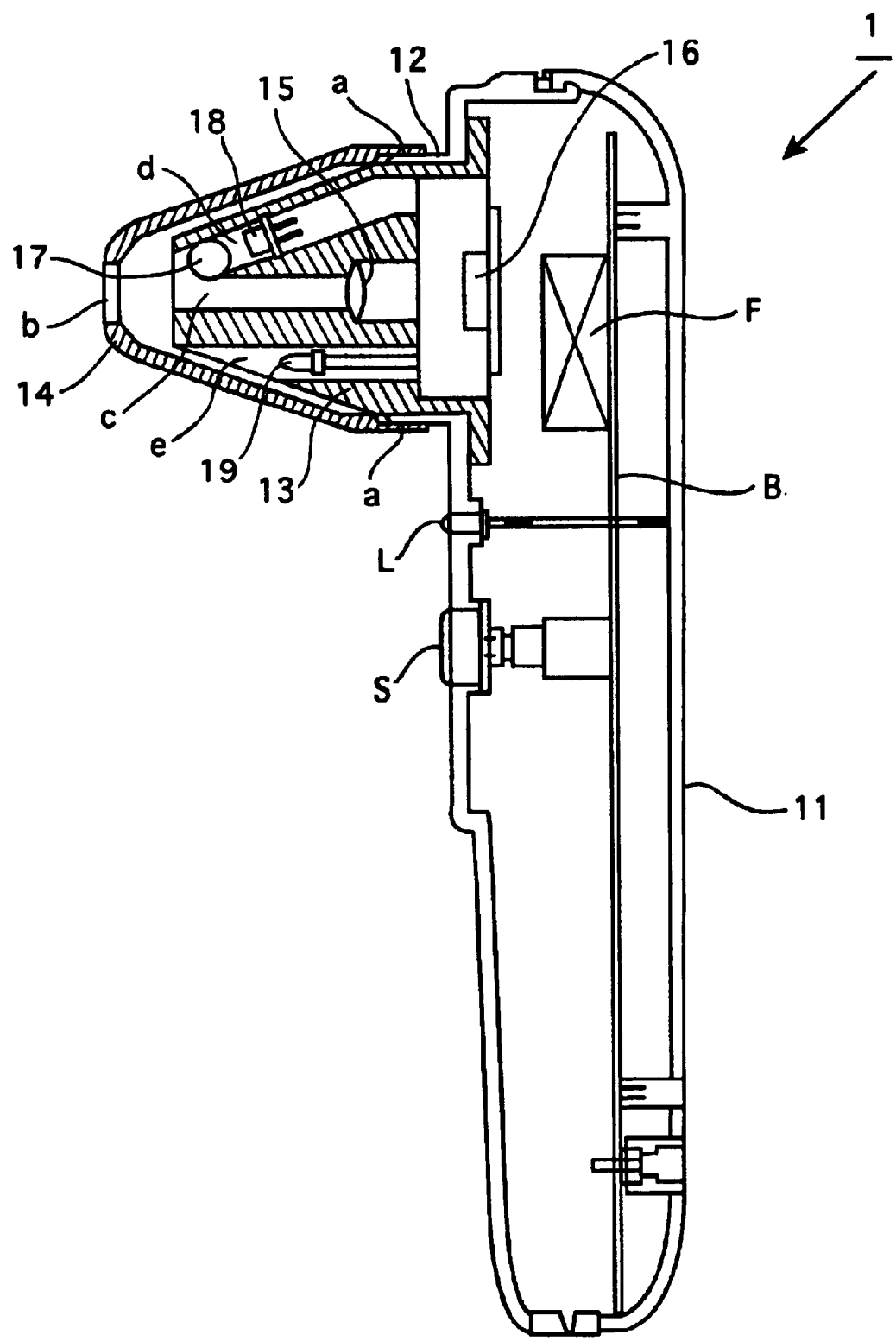
FIG. 3 is a longitudinal section of the laser beam projector.

Referring to the drawings, particularly to FIG. 1, a laser beam projector 1 according to one embodiment of the present invention is connected to a monitor television 3 by an electric cord 2, and to an AC adapter 5 by another electric cord 4.

The laser beam projector 1 has a casing 11 having a circular through hole formed at its front, delimited by the annular projection 12. A heat sink 13 having a trapezoid shape in section is fixed to the casing 11 by being inserted into the circular through hole with its base retained by the circumference of the circular through hole and supported by the annular projection 12.

The casing 11 has a mounting plate B fixed inside. An on-and-off control for controlling intermittent radiation of the laser beam, a laser driver and a video signal processing circuit (not shown) for the CCD camera 16 are mounted on the mounting plate B. Also, a cooling fan F, an LED lamp L and a push-button switch S are mounted on the mounting plate B. The cooling fan F may be omitted.

The LED lamp L comprises red and green LED chips, thus permitting radiation of red, green, yellow or amber by turning these LED chips on selectively or simultaneously.

The cooling fan F is placed behind the annular projection 12 for cooling the heat sink 13. The LED lamp L and the push-button switch S are fixed to the front of the casing 11.

The annular projection 12 has male threads "a" formed on its circumference, and a tapered cap 14 has female threads formed inside. The tapered cap 14 is attached to the annular projection 12 by mating the male threads of the annular projection 12 with the female threads of the tapered cap 14. The tapering shape of the tapered cap 14 facilitates the observing of a selected spot ahead of the tapered cap 14 by sight, and the user can aim the tapered cap 14 at the selected spot with accuracy. The tapered cap 14 may be so designed as to snap on the annular projection 12.

The tapered cap 14 has a laser beam opening "b" formed at its top end, and the laser beam projector is used by applying the tapered cap 14 to a selected spot on the skin with the laser beam opening "b" surrounding with the selected spot.

The tapered cap 14 occupies a part of the adjustable space between the skin and the heat sink 13. Specifically the distance from the skin to the front of the heat sink 13 can be adjusted by rotating the tapered cap 14, that is, driving the screw "a" of the tapered cap 14. In case of removing undesired hair from skin, such undesired hair is preferably removed by using depilatory cream or a razor prior to radiation of the laser beam, but the undesired hair can also be removed directly by means of the laser beam without removing the undesired hair beforehand.

The heat sink 13 has a channel "c" formed at its center, and a magnifying lens 15 is placed deep in the channel "c", and is directed to the laser beam opening "b", and the focal plane of the CCD camera 16 placed behind the magnifying lens 15.

The optical axis of the CCD camera 16 is aligned with the center line of the channel "c" and the center of the laser beam opening "b".

Another channel "d" is formed adjacent to the channel "c" at an oblique angle relative to the center line of the heat sink 13, and a spherical lens 17 is fitted on the front end of the oblique channel "d" and directed to the laser beam opening "b". The laser diode 18 is located behind the spherical lens 17 in the oblique channel "d".

Thus, a laser beam is projected obliquely form the laser diode 18 to the laser beam opening "b".

Still other channels "e" are made around the center channel "c", and high-intensity, white-light emission diodes 19 are placed in these channels "e". The light emission diodes 19 may be the ones capable of emitting yellow light.

Thus, beams of high-intensity, white light emission diodes 19 are projected from the circumference of the channel "c" to the laser beam opening "b" for illumination.

The heat sink 13 permits dissipation of the heat generated by the laser diode 18 by thermal conduction, thereby preventing the lowering of the efficiency of the laser diode 18.

The heat sink is made of a thermally conductive aluminum or aluminum alloy, and it has several channels made for dissipation of the heat generated inside.

The spherical lens 17 collects the light from the laser diode 18 to converge the light, forming a beam waist at its focal point. The spherical lens 17 has a short focal distance, and accordingly the depth of focus is so short that the power of light may be converged into a limited space.

The light diverges beyond the focal point, thus distributing the light power widely.

Thus, the thermal energy of the laser beam is lowered drastically beyond the focal point, and therefore, there is no fear of damaging the living body even though it is exposed to the laser beam by mistake.

The laser diode 18 may be a P-N junction diode of a chemical semiconductor such as GaAs, and it is driven by making an electric current flow directly in the P-N junction to produce a laser beam. The laser beam has a peak-to-peak wave length of 600 to 1,600 nm, and an optical output of 5 mw to 3 w. A single laser diode suffices to provide a required optic-to-thermal effect in a selected spot on the skin.

In addition to the optic-to-thermal effect, there can be caused the optic-to-electric effect, the optic-to-magnetic effect, the optic-to-dynamics effect, the optic-to-chemical effect, the optic-to-immunity effect, the optic-to-ferment effect, and such likes, and the metabolism in the living organisms is expedited by the optical biological activation, and accordingly circulation of the blood is improved. The laser beam is hardly absorbed by water or blood, and accordingly it can reach deep under the skin.

The push button switch S controls the on-and-off turning of the power supply, and its controlled depression changes the on-time of the intermittent radiation of the laser beam.

A touch-sensitive switch may be attached to the tapered cap 14 of the laser beam projector to detect when the tapered cap 14 is put in contact with the skin, thereby making the power supply turn on automatically when the tapered cap 14 is put in contact with the skin, and turn off automatically when the tapered cap 14 is removed from the skin.

This arrangement assures that no laser beam radiated unless the tip end of the tapered cap 14 of the laser beam projector is applied to the skin, and therefore, the laser beam cannot be thrown for instance, into the eye. Thus, safety is assured.

Each and every push of the push button switch S permits a series of mode switching operations to be effected sequentially from the turning-on of the power supply, the resetting of the length of "on"-time (one to six second long), and the turning-off of the power supply.

The color of the LED lamp L which shows the mode of the laser beam changes in the order of continuous green, intermittent green, continuous amber, intermittent amber, continuous red, and intermittent red as the length of "on"-time changes stepwise from one to six second long period. Thus, the length of "on"-time, that is, the amount of the light power can be determined in terms of the color of the light emitted by the single LED lamp L.

Finally, the push button switch S is depressed a relatively long time (1.5 seconds) to make the power supply turn off, stopping radiation of the laser beam. The push button switch S may be replaced by a dialing type of rotary switch.

An associated timer controls the push button switch S at a predetermined interval of one or one and half seconds, allowing the power supply to continue to turn on one to six seconds, short enough to cause no damage on the skin by a single shot.

In use, the tapered cap 14 of the laser bean projector is applied to a selected spot on the skin for treatment while watching the monitor television 3, which shows an enlarge image of the selected spot for treatment.

On the screen a target zone appears to indicate where the laser beam will be projected.

The laser beam projector is moved on the skin until discolored pigment cells or pores to be treated enter the target zone, and then, the push button switch S is depressed to throw the laser beam to the spot of discolored pigment cells or pores.

When the push button switch S is depressed, the laser diode 18 is made to turn on one second long, and off one second long. The on-and-off switching is repeated automatically, thereby radiating the laser beam intermittently.

When it is desired that the "on"-time is changed to control the amount of light power, the push button switch S is depressed repeatedly to increase the "on"-time step by step until the desired length of "on"-time has been reached, and then, depression of the push button switch S is made to cease.

When occasion demands, the throwing of the laser beam can be continued. An emergency switch may be provided to stop the throwing of the laser beam for safety.

As described above, the head of a laser beam projector has a laser beam opening made at its tip end, and the head has a heat sink installed therein. The heat sink has a channel formed at its center. A CCD camera is placed deep in the opening. A semiconductor laser source is so mounted in the heat sink that it may be inclined relative to the center line of the heat sink, and a condenser lens is placed ahead of the semiconductor laser source to make the laser beam diverge to the laser beam opening, and at the same time, the laser beam opening is illuminated with the light from one or more light sources.

With this arrangement an enlarged image of a selected spot of the skin can be given, thereby permitting the laser beam to be thrown at the spot with accuracy.

The CCD camera is placed deep in the center channel, thus shielding the CCD camera effectively from the surrounding light. Illumination of the laser beam opening by the light source gives the light to the CCD camera, thus providing a clear image of the spot on the focal plane of the camera.

The CCD camera is placed deep in the center channel, thereby minimizing the amount of light reflecting from the vicinity of the right spot. Thus, the degree of halation is reduced to a possible minimum.

As the CCD camera id directed at the laser beam channel, the distance between the camera and the center of the laser beam channel is little different from the distance between the camera and the circumference of the laser beam channel, and therefore, the image of the laser beam channel can be focused on the focal plane of the camera in spite of the short depth of focus.

As the semiconductor laser source is located on an oblique line relative to the center line of the heat sink, the light reflecting from the vicinity of the right spot is prevented effectively from falling on the CCD camera, and therefore, a clear image of the right spot can be provided.

The user can depress the push button switch to project a laser beam to the right spot exactly while watching the image of the right spot taken by the CCD camera.

Accordingly the treatment effect can be increased, reducing the danger of damaging the vicinity of the right spot by near miss.

Once the laser beam has been thrown at a right spot, the spot thus hit changes in appearance to confirm completion of the treatment on the spot, thus permitting a quick shift to a subsequent treatment.

The enlarged image of a selected area of skin permits the user to realize in what condition it is.

The laser beam projector has the drive circuit for the semiconductor laser source and the video signal processor circuit for the CCD camera installed in its housing.

The laser beam projector, therefore, can be put in operation simply by connecting it to a television, and all required operations can be performed without using any extra device other than the laser beam projector.

The laser beam projector has the connector to connect the CCD camera to a home television for presenting images of spots for treatment on its screen.

No television for exclusive use is required, and images of spots to be treated can be given on the large-sized screen of a home television.

The laser beam projector has the cooling fan placed behind the heat sink, on which the semiconductor laser source is mounted.

Even if the semiconductor laser source used should produce an increased mount of heat, the so produced heat can be removed effectively.

What is claimed is:

1. A laser beam projector, comprising:

a head having a tip to be applied to the skin of the user, said head having a heat sink provided therein and said tip defining a laser beam opening formed therein, said heat sink having a channel at its center;

a CCD camera placed at the end of said channel and directed toward said laser beam opening;

a semiconductor laser beam source attached to said heat sink such that it projects a laser beam at an oblique angle relative to the center line of said head;

a condenser lens situated ahead of said semiconductor laser beam source to converge the laser beam to said laser beam opening;

an illuminated source attached to said heat sink to illuminate said laser beam opening;

a drive circuit for said semiconductor laser beam source; and a video signal processing circuit for said CCD camera.

2. The laser beam projector as defined in claim 1, further comprising:

a connector for providing home television with the images taken by said CCD camera.

3. The laser beam projector as defined in claim 1, further comprising:

a cooling fan situated behind said heat sink.

* * * * *